(12) United States Patent
Consiglio et al.

(10) Patent No.: US 9,999,778 B2
(45) Date of Patent: Jun. 19, 2018

(54) NON-MAGNETIC HIGH VOLTAGE CHARGING SYSTEM FOR USE IN CARDIAC STIMULATION DEVICES

(75) Inventors: Ronald P. Consiglio, Clermont, FL (US); Harold J. Cates, Orlando, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 120 days.

(21) Appl. No.: 13/388,547

(22) PCT Filed: Jul. 9, 2010

(86) PCT No.: PCT/IB2010/053152
§ 371 (c)(1),
(2), (4) Date: Feb. 2, 2012

(87) PCT Pub. No.: WO2011/018720
PCT Pub. Date: Feb. 17, 2011

(65) Prior Publication Data
US 2012/0130224 A1    May 24, 2012

Related U.S. Application Data

(60) Provisional application No. 61/232,813, filed on Aug. 11, 2009.

(51) Int. Cl.
*A61N 1/39* (2006.01)
*A61B 5/055* (2006.01)
*A61N 1/37* (2006.01)

(52) U.S. Cl.
CPC .......... *A61N 1/3931* (2013.01); *A61N 1/3975* (2013.01); *A61N 1/3718* (2013.01); *A61N 1/3981* (2013.01)

(58) Field of Classification Search
CPC combination set(s) only.
See application file for complete search history.

(56) References Cited

U.S. PATENT DOCUMENTS

| 1,863,345 A | 6/1932 | Nicolson |
| 3,241,555 A | 3/1966 | Caywood et al. |
| 3,389,704 A | 6/1968 | Buchowski et al. |
| (Continued) | | |

FOREIGN PATENT DOCUMENTS

GB    2159003 A    11/1985

OTHER PUBLICATIONS

Noliac, "Rosen Transformers" at http://www.noliac.com/Rosen_transfornners-112.aspxviewed on Jan. 23, 2012.
(Continued)

*Primary Examiner* — Serkan Akar
*Assistant Examiner* — Farshad Negarestan

(57) ABSTRACT

A cardiac defibrillator comprises electrical wires or terminals (24) connected with or configured to connect with defibrillation electrode pads (22), and an electrical circuit (32, 32a, 32b) including an electrical storage element (52) and a piezoelectric transformer (50) arranged to charge the electrical storage element to a voltage effective for delivering a cardiac defibrillation shock. The electrical circuit is configured to discharge the electrical storage element across the electrical wires or terminals to deliver a cardiac defibrillation shock to the electrical wires or terminals.

13 Claims, 4 Drawing Sheets

(56) References Cited

U.S. PATENT DOCUMENTS

Figure 1:
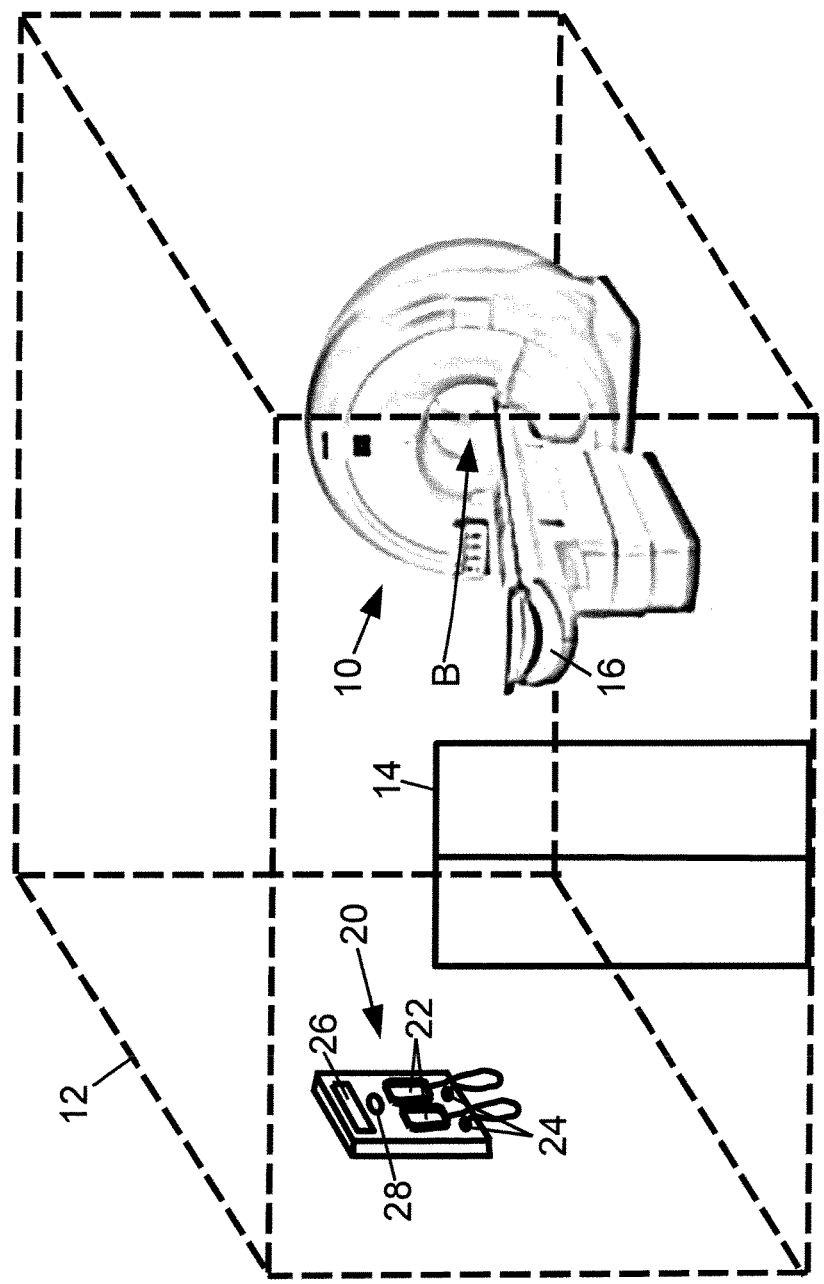

| | | | |
|---|---|---|---|
| 3,442,269 A | | 5/1969 | Druz |
| 3,778,648 A | | 12/1973 | Kawada |
| 3,836,794 A | | 9/1974 | Shimizu et al. |
| 4,054,806 A | | 10/1977 | Moriki et al. |
| 4,300,096 A | | 11/1981 | Harrison et al. |
| 4,390,840 A | | 6/1983 | Ganssen et al. |
| 4,459,505 A | | 7/1984 | Lim |
| 4,534,358 A | | 8/1985 | Young |
| 4,566,457 A | * | 1/1986 | Stemple .................. 607/5 |
| 4,651,099 A | | 3/1987 | Vinegar et al. |
| 4,678,996 A | | 7/1987 | Haacke et al. |
| 4,973,876 A | * | 11/1990 | Roberts ............... 310/316.01 |
| 6,141,584 A | | 10/2000 | Rockwell et al. |
| 6,151,232 A | * | 11/2000 | Furuhashi et al. ............ 363/97 |
| 2001/0038291 A1 | * | 11/2001 | Charneau et al. ............ 324/662 |
| 2002/0138103 A1 | | 9/2002 | Mulhauser et al. |
| 2003/0204217 A1 | | 10/2003 | Greatbatch |
| 2003/0220578 A1 | * | 11/2003 | Ho et al. .................. 600/521 |
| 2004/0215243 A1 | | 10/2004 | Houben et al. |
| 2004/0215279 A1 | | 10/2004 | Houben et al. |
| 2005/0281061 A1 | * | 12/2005 | Radecker et al. ......... 363/21.02 |
| 2008/0161886 A1 | * | 7/2008 | Stevenson ............... A61N 1/05 607/60 |

OTHER PUBLICATIONS

Steiner & Martins, Inc.; "Multi Layer Piezoelectric Transformer" at http://www.steminc.com/piezo/SMMTF55P6S50.asp viewed on Jan. 23, 2012.

Wikipedia; "Automated External Defibrillator" at http://en.wikipedia.org/wiki/Automated_external_defibrillator viewed on Jan. 23, 2012.

* cited by examiner

NON-MAGNETIC HIGH VOLTAGE CHARGING SYSTEM FOR USE IN CARDIAC STIMULATION DEVICES

CROSS REFERENCE TO RELATED APPLICATIONS

This application claims the benefit of U.S. provisional application Ser. No. 61/232,813 filed Aug. 11, 2009, which is incorporated herein by reference.

The following relates to the medical arts, magnetic resonance arts, and related arts.

Magnetic resonance (MR) is a useful technique for performing medical diagnoses such as MR imaging and MR spectroscopy. These techniques employ an MR scanner including a main magnet that generates a static magnetic field typically in a range of 0.1-7.0 Tesla, although higher or lower magnetic fields are usable. The main magnet is typically an electromagnet employing resistive or superconducting windings, and can have various configurations such as solenoidal, open-bore vertical, or so forth. Further electromagnets are configured to operate as magnetic field gradient coils so as to selectively superimpose magnetic field gradients on the static ($B_O$) magnetic field. Optional shim coils impose shim magnetic fields on the static ($B_O$) magnetic field. A radio frequency sub-system is configured to (i) generate a radio frequency electromagnetic field at a magnetic resonance frequency in order to excite magnetic resonance in a subject and to (ii) receive a magnetic resonance signal from the subject responsive to the excitation. Various pulse sequences can be implemented by the magnetic field gradient coils and the radio frequency sub-system in order to generate magnetic resonance, spatially limit, encode, manipulate, or spoil the generated magnetic resonance, detect the magnetic resonance, and perform other MR imaging- or spectroscopy-related operations. The MR scanner generates substantial stray magnetic fields and radio frequency interference (RFI), and is typically housed in a dedicated MR room that is shielded to isolate the MR scanner from nearby electronic systems. Safety protocols are employed to limit the likelihood that magnetic materials will be brought into the MR room since such materials can be attracted toward the MR scanner magnet, sometimes with catastrophic results. Under such protocols, MR can be safely and usefully employed for diverse medical applications.

However, some patients find MR imaging or spectroscopy to be a stressful procedure. An unfortunate consequence is that a patient undergoing an MR procedure may undergo cardiac arrest. In principle anyone can undergo cardiac arrest at any time; in practice, cardiac arrest is substantially more likely to occur in ill persons, elderly persons, hospital patients, and the like, and is more likely to occur when a person is undergoing a stressful experience such as being inserted into the closed or restricted bore of an MR scanner for an MR procedure that may reveal or illuminate a serious health problem. In short, a patient undergoing an MR procedure has a substantially elevated likelihood of undergoing cardiac arrest as compared with a member of the general population.

A patient undergoing cardiac arrest may be resuscitated using a cardiac defibrillator, such as an automated external defibrillator (AED). Immediate emergency response including rapid application of the defibrillator is known to be critical for successful patient resuscitation. It has been estimated that each minute of delay in delivering a defibrillation shock to a cardiac arrest victim reduces the chances of survival by 10 percent. See http://aed.com/faqs/#q03 (last accessed Jul. 24, 2009). In view of this urgency, even "non-medical" locations such as workplaces, schools, churches, and the like are encouraged to maintain an operational defibrillator so that in the event of a cardiac arrest the defibrillator can be immediately applied.

However, a defibrillator cannot be brought into the MR room, as this would violate safety protocols. Instead, a patient who undergoes cardiac arrest during an MR procedure is withdrawn from the MR scanner bore, transferred from the couch or other MR patient support apparatus onto a transport gurney, and wheeled out of the MR room to a location at which defibrillation can be safely applied to the patient. Precious seconds or minutes can be lost during this chain of operations, thus substantially reducing the likelihood of successful patient resuscitation. Cardiopulmonary resuscitation (CPR) may advantageously be applied during patient transfer, but it is difficult to continuously apply CPR while transferring the patient from within the MR scanner bore to a location where defibrillation may be applied. It is also known that CPR typically does not resuscitate a patient undergoing cardiac arrest, but merely provides some blood flow to the brain and other vital organs that delays the onset of tissue damage. Moreover, applying CPR to frail or elderly patients can cause contusions, rib fracture, or other physical trauma.

The following provides new and improved apparatuses and methods which overcome the above-referenced problems and others.

In accordance with one disclosed aspect, a cardiac defibrillator comprises electrical wires or terminals connected with or configured to connect with defibrillation electrode pads, and an electrical circuit including an electrical storage element and a piezoelectric transformer arranged to charge the electrical storage element to a voltage effective for delivering a cardiac defibrillation shock, the electrical circuit configured to discharge the electrical storage element across the electrical wires or terminals to deliver a cardiac defibrillation shock to the electrical wires or terminals.

In accordance with another disclosed aspect, the cardiac defibrillator of the immediately preceding paragraph further comprises automatic control circuitry configured to: (i) determine a cardiac state based on an electrocardiographic (ECG) signal received at the electrical wires or terminals; and (ii) operate the electrical circuit to deliver a cardiac defibrillation shock to the electrical wires or terminals conditional upon the determined cardiac state being indicative of cardiac arrest, wherein the cardiac defibrillator defines an automated external defibrillator (AED).

In accordance with another disclosed aspect, a cardiac defibrillator comprises electrical wires or terminals connected with or configured to connect with defibrillation electrode pads, and an electrical circuit including an electrical storage element and a transformer that does not contain any magnetic material and is arranged to charge the electrical storage element to a voltage effective for delivering a cardiac defibrillation shock, the electrical circuit configured to discharge the electrical storage element across the electrical wires or terminals to deliver a cardiac defibrillation shock to the electrical wires or terminals.

In accordance with another disclosed aspect, a magnetic resonance facility comprises a magnetic resonance scanner, a shielded room containing the magnetic resonance scanner, and a cardiac defibrillator as set forth in any one of three immediately preceding paragraphs disposed in the shielded room.

In accordance with another disclosed aspect, a device comprises electrical wires or terminals configured to electrically communicate with a heart, and an electrical circuit including an electrical storage element and a piezoelectric transformer arranged to charge the electrical storage element, the electrical circuit configured to discharge the electrical storage element across the electrical wires or terminals to deliver an electrical stimulation to the heart.

One advantage resides in providing an MR-compatible defibrillator. Another advantage resides in reducing delay between onset of cardiac arrest of a patient undergoing an MR procedure and initiation of potentially lifesaving cardiac defibrillation.

Another advantage resides in providing an electrical device for electrical stimulation of the heart that is substantially insensitive to magnetic fields.

Further advantages will be apparent to those of ordinary skill in the art upon reading and understanding the following detailed description.

FIG. 1 diagrammatically illustrates an MR facility including an MR scanner disposed in a shielded room that also contains a cardiac defibrillator.

Figure 2:
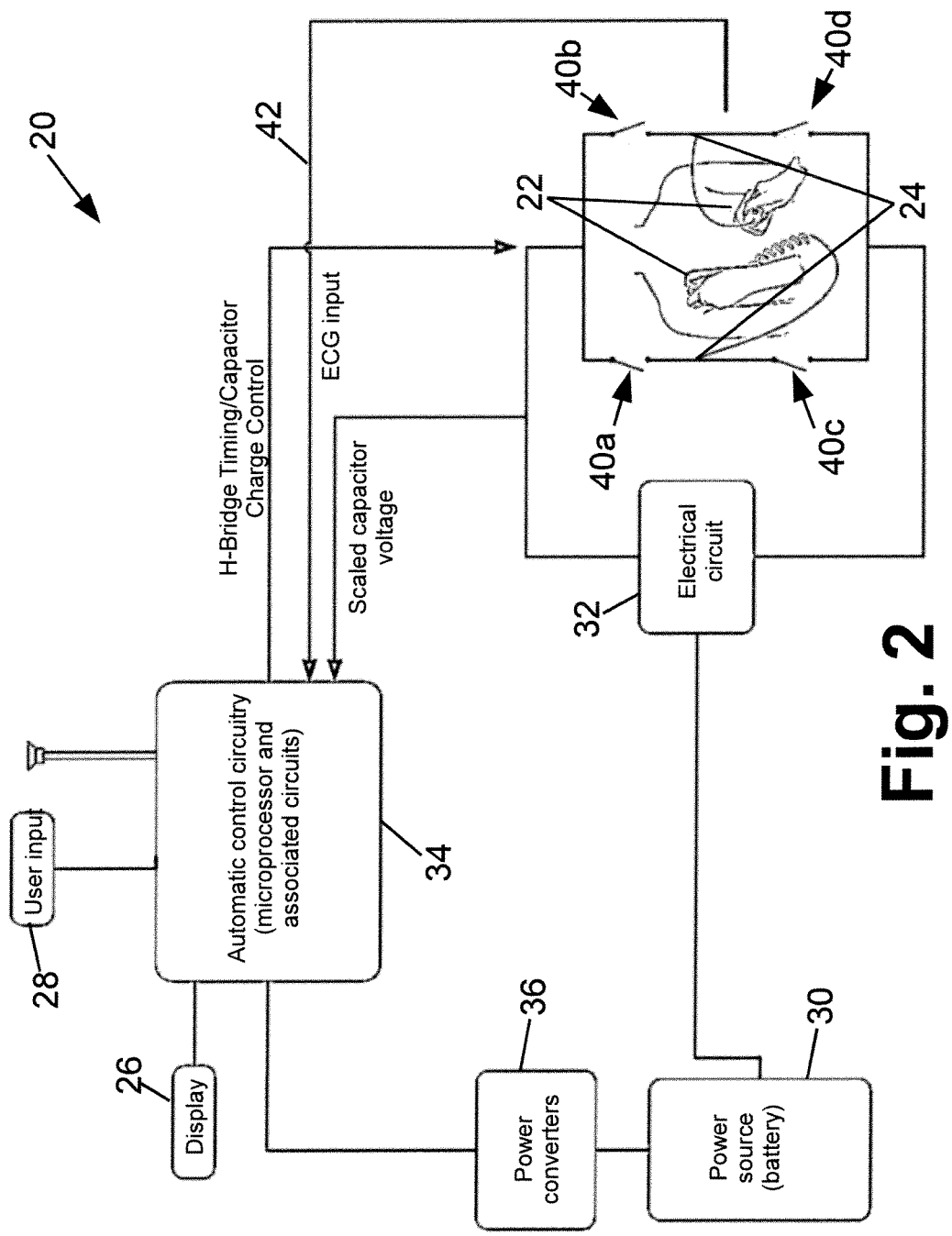

FIG. 2 diagrammatically illustrates the defibrillator of FIG. 1.

Figure 3:
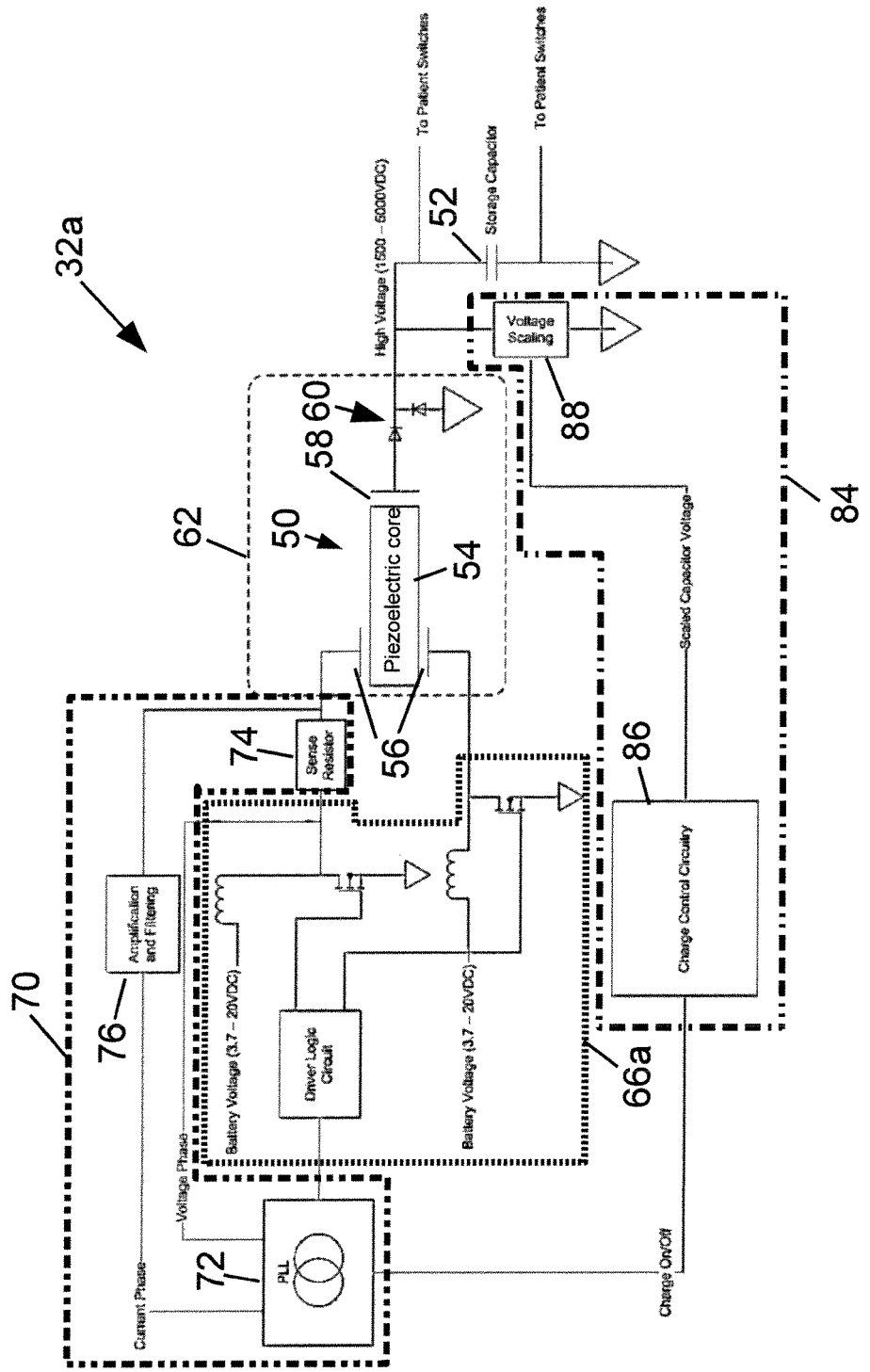
Figure 4:
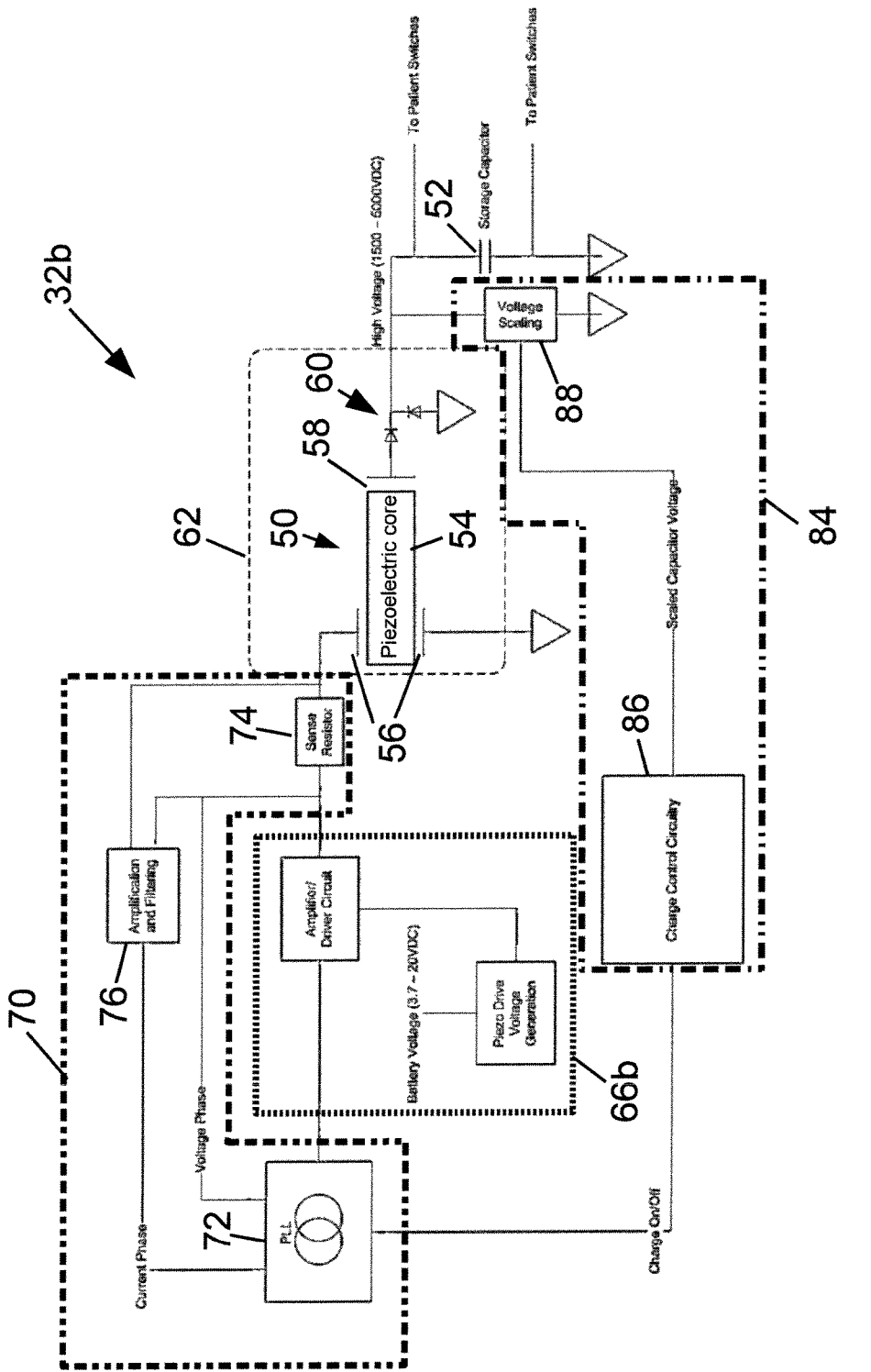

FIGS. 3 and 4 diagrammatically illustrate suitable embodiments of the electrical circuit of FIG. 2.

With reference to FIG. 1, a magnetic resonance facility includes a magnetic resonance (MR) scanner 10 disposed in a shielded room 12 (diagrammatically indicated in FIG. 1 as a dashed box). The illustrated magnetic resonance scanner 10 is an Achieva™ MR scanner available from Koninklijke Philips Electronics N.V. (Eindhoven, the Netherlands); however, substantially any MR scanner can be used. As is known in the art, the MR scanner 10 generates a strong magnetic field within a bore B of the MR scanner 10. The magnetic field in the bore depends upon the design of the MR scanner 10, but is typically in a range of about 0.1 Tesla and 7.0 Tesla or higher. Stray magnetic fields are also expected to extend a substantial distance outside of the bore B. The MR scanner 10 is also sensitive to radio frequency interference (RFI), and may also generate RFI that could disturb other neighbouring electronic systems. The shielded room 12 provides electromagnetic shielding against RFI, and optionally also includes magnetic shielding to prevent stray magnetic fields from penetrating beyond the confines of the shielded room 12. A door or other entrance 14 provides access to the shielded room 12. While the single entrance 14 is illustrated, multiple entrances are also contemplated. An imaging subject is brought through the entrance 14 to the MR scanner 10, and is placed on a couch or other subject support 16 of the MR scanner 10. The subject support 16 typically includes a translatable pallet (not illustrated in detail) that enables the subject disposed on the subject support 16 to be translated into, and precisely positioned within, the bore B for MR imaging, MR spectroscopy, or another MR procedure.

Preferably, a safety protocol dictates what items are permitted in the shielded room 12. The safety protocol excludes any item that includes magnetic material, due to a likelihood that the magnetic material that could detrimentally interact with the MR scanner 10. The safety protocol also extends to medical patients, medical screening subjects, veterinary subjects, inanimate subjects such as archaeological mummies, or other subjects that may be selected to undergo an MR procedure using the MR scanner 10. A typical safety protocol for a medical facility may include: (1) questioning the subject regarding any possible surgical implants (such as a pacemaker, orthopaedic implant, or so forth); (2) requiring removal of all metal objects from the patient before entering the shielded room 12; and (3) employing a metal detector (not shown) at the entrance 14 to detect any metal that may have been inadvertently missed by procedures (1) and (2). The foregoing safety protocol is intended to eliminate not only magnetic material but more generally any metal or other electrically conductive material, since an electrically conductive material disposed in the bore B can support eddy currents generated by time-varying magnetic fields which can cause heating and possibly injure the subject.

The illustrated MR facility also includes a cardiac defibrillator 20. A cardiac defibrillator is an instrument configured to deliver a cardiac defibrillation shock to a patient undergoing cardiac arrest. Toward this end, the cardiac defibrillator 20 includes a pair of electrode pads 22 connected with or configured to connect with the cardiac defibrillator 20 via electrical wires or terminals 24. The electrode pads 22 are configured to make external electrical contact with a torso, and optionally include an adhesive or other securing feature (not illustrated) for secure attachment to a torso. The torso is typically a human torso as in the case of a person undergoing cardiac arrest, although a canine, feline, or other torso is also contemplated as in the case of an veterinary subject undergoing cardiac arrest. The number of electrode pads 22 (and hence the number of corresponding electrical wires or terminals 24) is typically two, in order to enable delivery of a defibrillation shock across a subject torso; however, the use of three or more electrode pads (and corresponding electrical wires or terminals) is also contemplated, for example in order to deliver a desired pattern of electrical shock. The electrical wires or terminals 24 can comprise electrical connectors (e.g., sockets or the like) at which cables of the electrode pads 22 detachably connect (as in the case of modular or replaceable electrical pads), or can be electrically conductive wires that are permanently secured to and in electrical contact with the electrode pads 22 (as in the case of "hard-wired" electrode pads).

The illustrated cardiac defibrillator 20 is an automated external defibrillator (AED). An AED is a cardiac defibrillator that includes electrical circuitry configured to (i) determine a cardiac state based on electrical signals received at the electrical terminals 24 via the electrode pads 22, and (ii) deliver a cardiac defibrillation shock across the electrical terminals 24 condicational upon the determined cardiac state being indicative of cardiac arrest. The illustrated AED also includes a user interface, in the form of a display 26 in order to communicate operational instructions to a user. The user interface may, for example, inform the user of whether defibrillation is appropriate, and if so may instruct the user as to how to apply the defibrillation shock (for example, communicating to the user that no one should be touching the subject when the defibrillation shock is delivered). Instead of or in addition to the illustrated display 26, the user interface may include an audio speaker or other output device, and optionally may include one or more buttons, keys, or other user input devices. For example, in combination with the illustrated display 26 the AED 20 may include a button 28 that the user is to press in order to apply a defibrillation shock. The user interface may also employ a voice synthesizer to automatically verbally communicate operational instructions to the user.

With continuing reference to FIG. 1 and with further reference to FIG. 2, the cardiac defibrillator 20 includes a power source, namely a battery 30 in the illustrative example, that drives an electrical circuit 32 that develops a voltage effective for delivering a cardiac defibrillation shock, and discharges the voltage over the electrical wires or terminals 24 in order to deliver a cardiac defibrillation shock across the electrical wires or terminals. As disclosed herein, by constructing the electrical circuit 32 to be non-magnetic (that is, to use no magnetic materials, and in particular no ferromagnetic materials) the cardiac defibrillator 20 is made MR compatible and can be stored in the shielded room 12 containing the MR scanner 10. In the illustration of FIG. 1, the cardiac defibrillator 20 is mounted on an interior wall of the shielded room 12 in order to be both out-of-the-way and yet also immediately accessible in the event that a patient undergoes cardiac arrest. Other mounting arrangements are also contemplated, such as disposing the cardiac defibrillator on a table or so forth.

To implement automated aspects of the illustrative AED 20, automatic control circuitry 34 is powered by the battery 30 via suitable power converters 36, and is configured to (i) determine a cardiac state based on electrical signals received at the electrical wires or terminals 24 and (ii) operate the electrical circuit 32 to deliver a cardiac defibrillation shock across the electrical wires or terminals 24 condicational upon the determined cardiac state being indicative of cardiac arrest. The illustrative automatic control circuitry 34 is embodied as a microprocessor or microcontroller with associated circuitry such as: one or more memory chips; a read-only memory (ROM), eraseable ROM (EPROM), or the like storing firmware instructions to be executed by the microprocessor; an analog-to-digital (A/D) converter for reading the ECG signal; or so forth.

In order to enable the electrical wires or terminals 24 to operate both as sensor leads for determining the cardiac state and as electrical conductors for delivering the defibrillation shock, switches 40a, 40b, 40c, 40d selectively connect the electrical wires or terminals 24 with either the electrical circuit 32 (for delivering a defibrillation shock) or an electrocardiograph (ECG) input 42 of the automatic control circuitry 34.

In operation, the automatic control circuitry 34 sets the switches 40a, 40b, 40c, 40d to connect the ECG input 42 with the electrical wires or terminals 24 and analyzes the ECG to determine whether the subject is in cardiac arrest. If this analysis does indicate cardiac arrest, then the automatic control circuitry 34 causes the electrical circuit 32 to operate to develop a voltage effective for delivering a cardiac defibrillation shock, informs the user via the display 26 that defibrillation should be applied, and optionally provides other instructions such as instructing the user not to touch the subject during defibrillation. When the electrical circuit 32 is charged, the automatic control circuitry 34 sets the switches 40a, 40b, 40c, 40d to connect the electrical circuit 32 to the wires or terminals 24, and causes the display 26 to tell the user to press the button 28 in order to apply a defibrillation shock. Upon the user pressing the button 28, the electrical circuit 32 discharges across the the wires or terminals 24 so as to deliver a defibrillation shock to the heart via the electrical wires or terminals 24 and the torso of the subject undergoing cardiac arrest. After the defibrillation shock is delivered, the automatic control circuitry 34 resets the switches 40a, 40b, 40c, 40d to reconnect the ECG input 42 with the electrical wires or terminals 24 and again analyzes the ECG to determine whether the subject is still in cardiac arrest. If the subject is still in cardiac arrest, the automatic control circuitry 34 again causes the electrical circuit 32 to operate to develop a voltage effective for delivering a cardiac defibrillation shock and proceeds to instruct the user to deliver another defibrillation shock.

The cardiac defibrillator 20 illustrated in FIGS. 1 and 2 is an AED. However, it is also contemplated for the cardiac defibrillator 20 to be a more conventional (or, alternatively, less automated) device that does not provide ECG monitoring and analysis or user instructions. For example, the cardiac defibrillator may omit the ECG, user interface components 26, 28, switches 40a, 40b, 40c, 40d, and may include simplified control circuitry sufficient to cause the electrical circuit 32 to develop a charge effective for delivering a cardiac defibrillation shock and to discharge across the wires or terminals 24 so as to deliver a defibrillation shock.

Inclusion of magnetic material in a defibrillator generally disqualifies the defibrillator from admittance into the shielded room 12 containing the MR scanner 10. This is due to concern that the magnetic material could detrimentally interact with the magnetic field of the MR scanner 10. For example, the magnetic material may be forcibly drawn into the bore B and collide with substantial force into the bore wall, thus causing damage to the MR scanner 10 and/or the defibrillator and/or injury to any subject that happens to be disposed in the bore B. Moreover, it is recognized herein that the defibrillator can fail to operate properly in the presence of a stray magnetic field. Indeed, a magnetic field as low as about 0.1 T can cause saturation of the iron core of a transformer, thus leading to failure of the defibrillator. Lower magnetic fields can produce abnormal transformer action and compromise operation of the defibrillator. Malfunction, or failure of a defibrillator when used during a cardiac arrest event is undesirable.

Accordingly, the cardiac defibrillator 20 includes little magnetic material, and preferably includes no magnetic material. In particular, the electrical circuit 32 does not employ a conventional transformer including a ferromagnetic core. Moreover, the electrical circuit 32 does not employ an air-core transformer, because an air-core transformer is not effective for rapidly developing a voltage effective for delivering a cardiac defibrillation shock.

With reference to FIGS. 3 and 4, two illustrative embodiments are shown of suitable electrical circuits 32a, 32b, either of which may be used as the electrical circuit 32 in the cardiac defibrillator 20 of FIGS. 1 and 2. In both illustrative electrical circuits 32a, 32b, a piezoelectric transformer 50 is arranged to charge an electrical storage element 52, namely a storage capacitor in the embodiment of FIG. 3, to a voltage effective for delivering a cardiac defibrillation shock. The piezoelectric transformer 50 advantageously does not contain any magnetic material, or any ferromagnetic material, and does not have a magnetic core that can be saturated by an ambient magnetic field. In general, piezoelectric transformers are not attracted to or affected by the strong magnetic fields. A piezoelectric transformer includes a ceramic material or other material or assembly of materials (e.g., a multilayer structure) that exhibits or exhibit a strong piezoelectric effect. This material or assembly of materials exhibiting a strong piezoelectric effect is referred to herein as a piezoelectric core 54. An input a.c. electrical voltage is applied via piezoelectric transformer input terminals 56 to the piezoelectric core 54. The strong piezoelectric effect of the piezoelectric core 54 converts the input a.c. electrical voltage into mechanical vibration. At an output terminal 58 also coupled with the piezoelectric core 54, these vibrations are converted back into a higher voltage electrical output which is the step-up piezoelectric transformer output. Some suitable piezoelectric transformers for use as the piezoelectric transformer 50 include: multilayer Rosen piezoelectric transformers available from Noliac North America (Atlanta, Ga., USA); piezoelectric transformers designed for LCD backlighting available from Panasonic Corporation of North America (Secaucus, N.J., USA); and ceramic multilayer piezoelectric transformers available from Steiner & Martins, Inc. (Miami, Fla., USA). Other piezoelectric transformers can also be used.

The higher voltage output of the piezoelectric transformer 50 is an a.c. voltage. A rectifier 60 is interposed between the piezoelectric transformer 50 and the electrical storage element 52 to rectify the a.c. output of the piezoelectric transformer 50 in order to provide d.c. voltage (possibly with a large ripple component) for charging the electrical storage element 52. The illustrative rectifier 60 is constructed of two high-voltage diodes, but other rectifier topologies are also contemplated, including both half-wave rectifier and full-wave rectifier topologies. A voltage charging unit 62 comprising the piezoelectric transformer 50 and rectifier 60 is optionally duplicated in parallel to provide greater charging capacity, or the entire circuit 32a, 32b can be duplicated for this purpose. The input a.c. electrical voltage supplied at the piezoelectric transformer input terminals 56 is generated by a driver sub-circuit. In the embodiment of FIG. 3, a driver sub-circuit 66a uses a push-pull topology utilizing two pull down MOSFET transistors and two air-core (and hence non-magnetic) energy storage inductors. Other driver topologies can also be used, such as a "class A" amplifier topology driver sub-circuit 66b employed in the illustrative electrical circuit 32b, which includes high side/low side MOSFET drivers. Yet another driver topology mentioned as a further example but not illustrated is a single MOSFET driver topology, again preferably employing only air core inductors to avoid inclusion of magnetic material in the driver circuit.

The input a.c. electrical voltage supplied at the piezoelectric transformer input terminals 56 is preferably at a resonant frequency of the piezoelectric core 54 to maximize voltage conversion efficiency. Toward this end, a frequency control sub-circuit 70 includes a phase-locked loop (PLL) 72, a sense resistor 74, and amplification and filtering components 76 that operate to ensure that the piezoelectric transformer 50 is kept close to resonance by controlling the frequency supplied to the driver circuit 66a, 66b. A suitable frequency control approach is to filter and amplify the primary drive waveform with a bandpass filter and generate a filtered, amplified signal from the sense resistor 74. The phase of the two input signals is compared and the frequency of the signal to the driver circuit 66a, 66b is adjusted. This control approach works because when the voltage and current are in phase the piezoelectric device 50 is being driven at its resonance frequency.

For completeness, each of FIGS. 3 and 4 also diagrammatically depict a portion 84 of the automatic control circuitry 34 including a charge control sub-circuit 86 and a voltage scaling sub-circuit 88. The charge control sub-circuit 86 operates to activate the charging of the electrical storage element 52 by causing the frequency control sub-circuit 70 to lock onto the resonance frequency of the piezoelectric transformer 50. Other approaches for turning the charging on or off are also contemplated. The voltage scaling sub-circuit 88 is placed in parallel across the electrical storage element 52 in order to control the magnitude of voltage to which the electrical storage element 52 is charged. For defibrillation, this voltage should be effective for delivering a cardiac defibrillation shock, and in some embodiments this voltage is in a range of 1500-5000 volts d.c., although higher or lower voltages are also contemplated.

With returning reference to FIG. 1, the cardiac defibrillator 20 is described with reference to the illustrative MR facility. However, it will be appreciated that the cardiac defibrillator 20 is useful in any setting in which the cardiac defibrillator 20 may encounter a substantial magnetic field. Moreover, while an external cardiac defibrillator is illustrated, it is to be understood that the cardiac defibrillator can also be an implanted defibrillator. Still further, the disclosed apparatuses are contemplated for use in other external or implantable electronic devices that electrically stimulate the heart, such as cardiac pacemakers, insofar as such devices can usefully employ an electrical circuit including an electrical storage element arranged to be charged and then discharged across electrical wires or terminals to deliver an electrical stimulation to the heart.

For example, in the case of an implantable cardiac pacemaker (not illustrated), the electrical wires or terminals are suitably in intimate contact with the heart (rather than being in contact via electrode pads 22 that make external electrical contact with the torso so as to deliver the cardiac defibrillation shock to the heart via the torso) and the voltage scaling sub-circuit is suitably configured to control the magnitude of voltage to which the electrical storage element is charged so as to deliver a lower-voltage electrical stimulation to the heart providing a cardiac pacemaking effect rather than defibrillation. Such an implantable cardiac pacemaker is substantially insensitive to magnetic fields, and accordingly is MR compatible and also enables the person in which the device is implanted to engage in other activities that may involve magnetic interaction, such as arc welding, working near high voltage power generation or transmission facilities, or so forth.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. An external cardiac defibrillator comprising:
    defibrillation electrode pads configured to make external electrical contact with a torso configured to deliver the cardiac defibrillation shock to the torso; and
    an electrical circuit including an electrical storage element, inductors including only air core inductors, and a piezoelectric transformer arranged to charge the electrical storage element to a voltage effective for delivering a cardiac defibrillation shock, the electrical circuit configured to discharge the electrical storage element across the defibrillation electrode pads to deliver a cardiac defibrillation shock to the defibrillation electrode pads;
    wherein the cardiac defibrillator does not contain any ferromagnetic material and is disposed externally of a patient.

2. The external cardiac defibrillator as set forth in claim 1, wherein the electrical storage element comprises a storage capacitor.

3. The external cardiac defibrillator as set forth in claim 1, further comprising:
    automatic control circuitry configured to (i) determine a cardiac state based on an electrocardiographic (ECG) signal received at the defibrillation electrode pads and (ii) operate the electrical circuit to deliver a cardiac defibrillation shock to the defibrillation electrode pads conditional upon the determined cardiac state being indicative of cardiac arrest, wherein the external cardiac defibrillator defines an automated external defibrillator (AED).

4. The external cardiac defibrillator as set forth in claim 3, further comprising:
a user interface by which the AED communicates operational instructions to a user.

5. The external cardiac defibrillator as set forth in claim 1, wherein the electrical circuit includes a plurality of piezoelectric transformers arranged to charge the electrical storage element to a voltage effective for delivering a cardiac defibrillation shock.

6. The external cardiac defibrillator as set forth in claim 1, wherein the electrical circuit comprises:
a driver circuit driving the piezoelectric transformer using a drive waveform; and
a frequency control sub circuit including a phase-locked loop (PLL), a sense resistor, and amplification and filtering components, the frequency control sub-circuit configured to maintain the piezoelectric transformer at a resonance frequency by controlling the driver circuit by filtering and amplifying the drive waveform with the amplification and filtering components to generate a filtered and amplified signal from the sense resistor, comparing the phase of the drive waveform and the filtered and amplified signal, and adjusting the frequency of the drive waveform based on the comparison to maintain the drive waveform voltage and current in phase.

7. The external cardiac defibrillator as set forth in claim 1, wherein the electrical circuit comprises a phase locked loop (PLL) configured to maintain the piezoelectric transformer at a resonance frequency.

8. The external cardiac defibrillator as set forth in any claim 1, wherein the electrical circuit comprises a rectifier electrically interposed between an output of the piezoelectric transformer and the electrical storage element.

9. An external cardiac defibrillator comprising:
defibrillation electrode pads configured to make external electrical contact with a torso configured to deliver a cardiac defibrillation shock to the torso;
an electrical circuit including an electrical storage element, inductors including only air core inductors, and a piezoelectric transformer that does not contain any magnetic material and is arranged to charge the electrical storage element to a voltage effective for delivering a cardiac defibrillation shock, the electrical circuit configured to discharge the electrical storage element across the defibrillation electrode pads to deliver a cardiac defibrillation shock to the defibrillation electrode pads; and
automatic control circuitry configured to (i) determine a cardiac state based on an electrocardiographic (ECG) signal received at the defibrillation electrode pads and (ii) operate the electrical circuit to deliver a cardiac defibrillation shock to the defibrillation electrode pads conditional upon the determined cardiac state being indicative of cardiac arrest, wherein the cardiac defibrillator defines an automated external defibrillator (AED);
wherein the external cardiac defibrillator does not contain any magnetic material and is disposed externally of a patient.

10. The external cardiac defibrillator as set forth in claim 9, wherein the electrical storage element comprises a storage capacitor.

11. The external cardiac defibrillator as set forth in claim 9, wherein the electrical circuit comprises a rectifier electrically interposed between an output of the piezoelectric transformer and the electrical storage element.

12. The external cardiac defibrillator as set forth in claim 9, wherein the piezoelectric transformer is arranged to charge the electrical storage element to a voltage in a range of 1500-5000 volts d.c.

13. A magnetic resonance facility comprising:
a magnetic resonance scanner;
a shielded room containing the magnetic resonance scanner; and
an external cardiac defibrillator disposed in the shielded room the external cardiac defibrillator including:
defibrillation electrode pads configured to make external electrical contact with a torso configured to deliver the cardiac defibrillation shock to the torso, and
an electrical circuit including an electrical storage element, inductors including only aft core inductors, and a piezoelectric transformer arranged to charge the electrical storage element to a voltage effective for delivering a cardiac defibrillation shock, the electrical circuit configured to discharge the electrical storage element across the defibrillation electrode pads to deliver a cardiac defibrillation shock to the defibrillation electrode pads;
wherein the external cardiac defibrillator does not contain any magnetic material and is disposed externally of a patient.

* * * * *